United States Patent
Shalaby et al.

(10) Patent No.: US 9,446,165 B2
(45) Date of Patent: *Sep. 20, 2016

(54) SWELLABLE FIBER AND MICROFIBER FORMING POLYETHER-ESTERS AND APPLICATIONS THEREOF

(71) Applicant: Poly-Med, Inc., Anderson, SC (US)

(72) Inventors: Shalaby W. Shalaby, Anderson, SC (US); James M. Lindsey, Pendleton, SC (US); Scott Taylor, Pendleton, SC (US); David E. Linden, Pendleton, SC (US); David R. Ingram, Central, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,779

(22) Filed: Jul. 21, 2014

(65) Prior Publication Data

US 2014/0328888 A1 Nov. 6, 2014

Related U.S. Application Data

(63) Continuation of application No. 11/820,849, filed on Jun. 20, 2007, now Pat. No. 8,784,861, which is a continuation-in-part of application No. 11/453,207, filed on Jun. 14, 2006, now Pat. No. 8,927,001.

(60) Provisional application No. 60/690,751, filed on Jun. 15, 2005.

(51) Int. Cl.

| | |
|---|---|
| *A61L 17/10* | (2006.01) |
| *A61L 17/14* | (2006.01) |
| *A61L 27/34* | (2006.01) |
| *A61L 29/08* | (2006.01) |
| *A61L 31/10* | (2006.01) |
| *A61L 31/06* | (2006.01) |
| *C08G 63/664* | (2006.01) |
| *A61L 17/00* | (2006.01) |
| *A61L 27/18* | (2006.01) |
| *A61L 27/54* | (2006.01) |
| *A61L 27/58* | (2006.01) |
| *C08G 63/668* | (2006.01) |
| *C08G 64/18* | (2006.01) |

(52) U.S. Cl.
CPC ............ *A61L 17/105* (2013.01); *A61L 17/005* (2013.01); *A61L 17/145* (2013.01); *A61L 27/18* (2013.01); *A61L 27/34* (2013.01); *A61L 27/54* (2013.01); *A61L 27/58* (2013.01); *A61L 29/085* (2013.01); *A61L 31/06* (2013.01); *A61L 31/10* (2013.01); *C08G 63/664* (2013.01); *C08G 63/668* (2013.01); *C08G 64/183* (2013.01); *Y10T 442/60* (2015.04)

(58) Field of Classification Search
None
See application file for complete search history.

(56) References Cited

U.S. PATENT DOCUMENTS

| | | | |
|---|---|---|---|
| 4,624,256 A | 11/1986 | Messier | |
| 5,123,912 A | 6/1992 | Kaplan | |
| 5,320,624 A | 6/1994 | Kaplan | |
| 5,543,158 A | 8/1996 | Gref | |
| 6,136,018 A | 10/2000 | Roby | |
| 6,498,229 B1 * | 12/2002 | Shalaby | C08G 63/08 525/411 |
| 8,784,861 B2 * | 7/2014 | Shalaby | A61L 17/145 424/423 |
| 8,927,001 B2 * | 1/2015 | Shalaby | A61L 17/145 424/423 |
| 2001/0000728 A1 | 5/2001 | Sawhney | |
| 2003/0162894 A1 | 8/2003 | Buchholz | |
| 2003/0162940 A1 | 8/2003 | Shalaby | |
| 2004/0171323 A1 * | 9/2004 | Shalaby | A01N 25/10 442/123 |
| 2005/0171299 A1 | 8/2005 | Shalaby | |

* cited by examiner

*Primary Examiner* — Brian Gulledge

(57) ABSTRACT

Biomedical and tissue engineering devices, such as surgical sutures and microporous scaffolds, respectively, which undergo swelling and increase in dimensions when placed in aqueous environments such as living tissues, are produced by the melt-spinning or electrostatic spinning into strong monofilament and multifilament yarns or microfibrous fabrics, respectively. Such devices are formed from especially high molecular weight crystalline polyether-esters having a minimum inherent viscosity of 0.8 dL/g and heat of fusion of at least 5 J/g, wherein the polyether-esters are made by grafting to a polyester component a polyether glycol component having a minimum molecular weight of about 11 kDa with at least one cyclic monomer.

12 Claims, No Drawings

US 9,446,165 B2

SWELLABLE FIBER AND MICROFIBER FORMING POLYETHER-ESTERS AND APPLICATIONS THEREOF

The present application is a continuation of U.S. application Ser. No. 11/820,849 filed Jun. 20, 2007 which is a continuation in part of patent application U.S. Ser. No. 11/453,207 filed on Jun. 14, 2006, which claims the benefits of prior provisional application U.S. Ser. No. 60/690,751 filed Jun. 15, 2005, which are hereby incorporated herein in their entireties by reference.

FIELD OF THE INVENTION

This invention is directed toward a swellable, absorbable polyether-ester with a sufficiently high molecular weight and degree of crystallinity to allow their conversion by melt-spinning or electrostatic spinning to produce strong monofilament yarns, multifilament yarns or non-woven microfibrous fabrics, respectively, for use in biomedical, pharmaceutical, and tissue engineering application devices. Such devices possess sufficiently low modulus and, in effect, low compliance to be biomechanically compatible when interfacing with living tissues. The composition of the constituent polymeric chains of these materials are tailored to allow the corresponding devices to undergo an increase in their compliance and dimension by swelling when placed in an aqueous environment, as in the case of living tissues.

BACKGROUND OF THE INVENTION

There have been described in prior disclosure U.S. patent application Ser. No. 11/175,636, as well as the present parent application, (1) absorbable amphiphilic block copolymeric compositions of polyether-esters having an inherent viscosity of at least 0.5 dL/g and a heat of fusion of at least 10 J/g, which can undergo swelling in an aqueous environment as a in living tissues due to water up-take of at least 10 percent of their original mass; and (2) that such amphiphilic block copolymeric compositions can be converted to complaint monofilament and multifilament braids. However, it has been discovered during the course of the study associated with the present invention, that in order to produce commercially useful and clinically competitive biomedical devices, such as surgical sutures, and tissue engineering scaffolds comprising swellable, absorbable, high strength, melt-spun monofilament and multifilament yarns or high strength electrostatically spun microfibrous, non-woven fabrics, the constituent amphiphilic polyether-esters must meet more stringent requirements than those disclosed earlier in terms of molecular weight and degree of crystallinity, which can be expressed in terms of inherent viscosity and heat of fusion, respectively. To prepare polyether-esters of sufficiently high molecular weight and degree of crystallinity to produce the required high strength melt-spun monofilament and multifilament yarns or electrostatically spun microfibers, while maintaining a sufficient degree of amphiphilicity to achieve clinically practical levels of swellability in the biological environment, the need to use polyether glycol intermediates having a minimum molecular weight of 11 kDa, was surprisingly uncovered during the course of the study associated with the present invention. This, in turn, demonstrates the novelty of the present invention when contrasted with a distantly relevant prior art, particularly US Publication No. 2007/0014848, where polyether intermediates, having a maximum molecular weight of 10 kDa, have been used to produce relatively lower molecular weight and in most cases, practically amorphous polyether-esters unsuitable for conversion into the yarns and microfibers.

SUMMARY OF THE INVENTION

Generally, the present invention is directed to a swellable, absorbable, fiber- or microfiber-forming, high molecular weight, crystalline polyether-ester having a (a) polyether chain component with a molecular weight of more than about 11 kDa; (b) an inherent viscosity of at least 0.8 dL/g in chloroform or hexafluoroisopropyl alcohol; and (c) heat of fusion exceeding 5 J/g, wherein the fibers or microfibers thereof undergo at least 0.5% increase in their cross-sectional area when placed in an aqueous environment as in living, soft tissues for less than three (3) hours, wherein the polyether-ester comprises a polyether glycol grafted with at least one cyclic monomer selected from the group consisting of l-lactide, ε-caprolactone, glycolide, p-dioxanone, trimethylene carbonate, and a morpholinedione, and wherein the polyether chain component of the polyether-ester is a polyethylene oxide. Alternatively, the polyether chain component of the polyether-ester is a block copolymer of polyethylene oxide and polypropylene oxide or is a random copolymer of ethylene oxide and propylene oxide.

Another aspect of this invention deals with a swellable, absorbable, fiber- or microfiber-forming, high molecular weight, crystalline polyether-ester having a (a) polyether chain component with a molecular weight of more than about 11 kDa; (b) an inherent viscosity of at least 0.8 dL/g in chloroform or hexafluoroisopropyl alcohol; and (c) heat of fusion exceeding 5 J/g, wherein the fibers or microfibers thereof undergo at least 0.5% increase in their cross-sectional area when placed in an aqueous environment as in living, soft tissues for less than three (3) hours, wherein the polyether-ester comprises a polyether glycol grafted with at least one cyclic monomer selected from the group consisting of l-lactide, ε-caprolactone, glycolide, p-dioxanone, trimethylene carbonate, and a morpholinedione, and wherein the polyether-ester is in the form of (1) a monofilament yarn made by melt-spinning and further converted to a surgical suture; (2) a multifilament yarn made by melt-spinning and further processed into a braided surgical suture; (3) a multifilament yarn and further processed into a compressible, microporous felt for use as a scaffold for tissue engineering; or (4) a non-woven, microporous, microfibrous fabric made by electrostatic spinning of a solution of said polyether-ester in an organic solvent or a mixture of solvents. It is also the objective of this invention that the monofilament suture matrix comprises at least one bioactive agent selected from the group of agents known for their antimicrobial, antineoplastic or tissue growth promoting activities, and when said suture is implanted in living tissues, exhibits a ratio of the percent breaking strength retention/absorption (measured in terms of mass loss, reduction in volume or reduction in cross-sectional area) at a given time period that is at least 5% lower than those established for the parent polyester of the polyester chain component of the respective polyether-ester.

A specific aspect of this invention deals with such a polyether-ester is in the form a monofilament yarn made by melt-spinning and further converted to a surgical suture that displays a breaking strength of more than 30 Kpsi and a modulus of less than 300 Kpsi, and more specifically, the modulus of the surgical suture decreases by at least 5% after less than 3 hours following its placement in an aqueous environment as in living tissues.

Preferably, the monofilament suture further comprises an absorbable coating, which includes at least one bioactive agent selected from the group of agents known for their antimicrobial, antineoplastic, or tissue growth promoting activities.

In another embodiment the polyether-ester is in the form of a multifilament yarn made by melt-spinning and further processed into a braided surgical suture that comprises an absorbable coating, which contains at least one bioactive agent selected from the group of agents known for their antimicrobial, antineoplastic, or tissue growth promoting activities.

In a clinically important aspect of this invention the polyether-ester is in the form of a multifilament yarn and further processed into a compressible, microporous felt for use as a scaffold for tissue engineering and the felt has an absorbable coating, which contains at least one bioactive agent selected from the group of agents known for their antimicrobial, antineoplastic, or tissue growth promoting activities.

DETAILED DESCRIPTION OF PREFERRED EMBODIMENTS

This invention generally is directed toward especially tailored, absorbable polyether-esters, which exhibit sufficiently high molecular weight and melt-viscosity to allow their eventual conversion to oriented, dimensionally stable monofilament and multifilament yarns suitable for use in constructing high strength surgical sutures or microporous felt for tissue engineering applications. This invention also discloses the general use of the especially tailored, high molecular weight crystalline polyether-esters, which can exhibit high viscosity solutions with low solute content, optimal for the electrospinning of high strength microfibrous constituents of microporous fabrics that can, in turn, be useful clinically as covers for wounds, ulcers, and scaffolds for tissue engineering as well as filters for cell fractionation. To meet the stringent requirements and for producing the aforementioned swellable constructs comprising high strength monofilament and multifilament yarns or electrospun microfibrous yarns, the present invention addresses equally stringent physicochemical requirements for the polyether-esters suitable for use in the eventual production of the swellable devices disclosed herein. These requirements include, but are not limited to, (1) using a polyether glycol having a molecular weight exceeding 11 kDa for grafting with at least one cyclic monomer to produce ABA-type block copolymer exhibiting a high molecular weight associated with an inherent viscosity of at least 0.8 dL/g for a dilute solution in chloroform or hexafluoroisopropyl alcohol (HFIP) of about 0.1 percent (weight/volume); (2) adjusting the polyether-to-polyester weight ratio in the chain so as to guarantee attaining the sought molecular weight without compromising the amphiphilicity level needed to achieve a minimum of 0.5 percent increase in fiber or microfiber cross-sectional area when in the presence of an aqueous environment as in living tissue for less than three hours; (3) selecting one or more monomer for end-grafting onto the polyether glycol as to yield crystalline products, which can be converted to devices that are dimensionally stable during critical processing steps and upon storage; (4) selecting combinations of a polyether-type, as in polyethylene glycol, and block or random copolymers of ethylene and propylene oxides as well as cyclic monomers known to provide a range of hydrolytic stability as glycolide (or a morpholine dione), lactide (or ϵ-caprolactone and trimethylene carbonate) to yield polyether-esters with unique absorption-strength retention profiles wherein the rates of breaking strength decay relative to the rates of absorption/mass loss are then those established for the traditional polyesters that are not part of a polyether-ester block copolymeric structure; (5) selecting the ring-opening polymerization charge and reaction conditions to insure the formation of the desired copolymeric chain structure and distribution of constituent repeat units, which, in turn, control the degree of crystallinity, as well as the thermal properties and solubility, which are pertinent to applied melt processing and electrospinning protocols; and (6) selecting the proper polyether/polyester ratios to allow optimal incorporation of a specific bioactive agent into the matrix of the fibrous or microfibrous constituents of the device.

Further illustrations of the present invention are provided by the following examples:

Example 1

Preparation and Characterization of Crystalline, Amphiphilic, Triblock Block Copolymer Having a Central Polyethylene Oxide and Polyester Terminal Blocks (P-I Series): General Method Predried crystalline, high molecular weight PEG is mixed, under nitrogen in a stainless steel reactor equipped for mechanical stirring, with the desired amount(s) of cyclic monomer(s) in the presence of stannous octanoate as a catalyst. The mixture is then heated to achieve complete dissolution of all reactants. The mixing is continued while heating to a polymerization temperature of 160 to 180° C. depending on the type and concentration of cyclic monomer(s). The reaction is maintained at that temperature while stirring until the product becomes too viscous to stir and essentially complete monomer conversion is achieved (8-10 hours depending on the type and concentration of cyclic monomer(s)). At this stage, polymerization is discontinued, the product is cooled, isolated, ground, dried, and traces of residual monomer are removed by distillation under reduced pressure using a temperature that is below the copolymer melting temperature ($T_m$), but not exceeding 110° C., or by precipitation.

The resulting copolymer is characterized for (a) molecular weight in terms of inherent viscosity (I.V.) and $M_n/M_w$ by GPC if the polymer is soluble in $CH_2Cl_2$; (b) $T_m$ and heat of fusion ($\Delta H_f$) using differential scanning calorimetry; (c) crystallinity using wide-angle X-ray diffraction.

Examples 2 to 10

Synthesis and Characterization of Specific Examples of Type P-I Block Copolymers (P-I-A to P-I-I)

Copolymers P-I-A to P-I-I are prepared and characterized following the general methods described in Example 1. The polymerization charge and properties of resulting polymers are summarized in Table I.

Example 11

Preparation and Characterization of Crystalline, Amphiphilic, Triblock Block Copolymer Having a Central Polyether Block Composed of a Block or Random Copolymer of Ethylene and Propylene Oxides and Polyester Terminal Blocks (P-II Series): General Method Predried, high molecular weight block or random copolymer of ethylene and propylene oxides is mixed under nitrogen in a stainless steel reactor equipped for mechanical stirring, with the desired amount(s) of cyclic monomer(s) in the presence of stannous octanoate as a catalyst. The mixture is then heated to achieve complete dissolution of all reactants. The mixing is continued while heating to a polymerization temperature of 140 to 180° C. depending on the type and concentration of cyclic monomer(s). The reaction is maintained at that temperature while stirring until the product becomes too viscous to stir and essentially complete monomer conversion is achieved (8-60 hours depending on the type and concentration of cyclic monomer(s)). At this stage, polymerization is discontinued, the product is cooled, isolated, ground, dried, and traces of residual monomer are removed by distillation under reduced pressure using a temperature that is below the copolymer melting temperature ($T_m$), but not exceeding 110° C., or by precipitation.

The resulting copolymer is characterized for (a) molecular weight in terms of inherent viscosity (I.V.) and $M_n/M_w$ by GPC if the polymer is soluble in $CH_2Cl_2$; (b) $T_m$ and heat of fusion ($\Delta H_f$) using differential scanning calorimetry; (c) crystallinity using wide-angle X-ray diffraction.

Examples 12 to 15

Synthesis and Characterization of Specific Examples of Type P-II Block Copolymers (P-II-A to P-II-D)

Copolymers P-II-A to P-II-D were prepared and characterized following the general methods described in Example 11. The polymerization charge and properties of resulting polymers are summarized in Table II.

Example 16

Preparation and Characterization of Crystalline, Amphiphilic Block Copolymer of Polyethylene Glycol (PEG) and Polyester Interlinked with Low $T_g$ Polymer Segments (P-III Series): General Method The general polymerization methods and polymer isolation, purification, and characterization of P-III series are implemented using analogous experimental protocols as those described in Example 1 for the P-I series with the exception of the following:

The PEG is first end-grafted with trimethylene carbonate (TMC) or a TMC or ε-caprolactone (CL) rich comonomer mixture at 150 to 180° C. (depending on the type and concentration of cyclic monomer(s)) until essentially complete monomer conversion is achieved yielding a PEG-Low $T_g$ Segment copolymer. At this point, the temperature is lowered to 140° C. and the monomeric precursor(s) of the crystalline hydrophobic component(s) are added and thoroughly mixed with the PEG-Low $T_g$ Segment copolymer. The reaction temperature is then raised to 140° C. to 160° C. depending on the type and concentration of cyclic monomer(s), and polymerization is continued.

Examples 17 to 23

Synthesis and Characterization of Specific Examples of Type P-III Block Copolymers (P-III-A to P-III-G)

Copolymers P-III-A to P-III-G were prepared and characterized following the general methods described in Example 16. Polymerization charge and properties of resulting polymers are summarized in Table III.

Example 24

Melt-Spinning of Typical Block Copolymers into Typical Monofilaments

The melt spinning of four typical block copolymers are accomplished using a ¾" extruder at the temperature noted in Table IV. The extrudates are oriented in two stages using the draw ratio/temperature noted in Table IV.

Example 25

Properties of Typical Oriented Monofilaments as Swellable Sutures

The initial tensile properties and breaking strength retention (BSR) properties of the monofilament sutures are determined using a MiniBionix MTS Universal Tester, Model 858. The simulated bioswelling properties are evaluated using a phosphate buffer at 37° C. and pH 7.4. The in vitro BSR properties are determined on sutures incubated in a phosphate buffer at 37° C. and pH 7.4. The in vivo BSR properties are determined on sutures after subcutaneous implantation in Sprague-Dawley rats. The accelerated in vitro mass loss properties are determined on sutures incubated in a phosphate buffer at 37° C. and pH 12.0. Properties of typical oriented monofilaments as swellable sutures are shown in Table V.

Example 26

Melt-Spinning of Typical Block Copolymers into Typical Multifilaments and Preparation of Braided Sutures Thereof The multifilament melt spinning of two typical block copolymers are accomplished using a multi-hold die, under slightly higher thermal conditions as compared to those used in the production of the monofilaments in Example 24. Depending on the copolymer type and required yarn denier, the extruded multifilament yarns are oriented in two stages at a temperature range of either 50 to 70° C. or 65° C. to 85° C. Block copolymers P-I-A and P-II-D are converted to braided multifilaments, and tested for their tensile properties using a MiniBionix MTS Universal Tester, Model 858. Braided multifilaments of block copolymers P-I-A and P-II-D, with diameters of 0.45 and 0.32 mm respectively, exhibit tensile strengths of 40.0 and 52.7 Kpsi and elongations of 48% and 24% respectively.

Example 27

Preparation and Electrospinning of Typical Block Copolymers

Electrospinning is accomplished on an electrospinning unit constructed in-house from the polymers listed in Table I below. Solutions were prepared by dissolving 10-30 w/v % polymer, depending on the polymer molecular weight and desired fiber diameter, in a mixture of 1:1 dichloromethane:chloroform. Electrospinning is conducted using the following conditions: +10-25 kV charge at needle tip, −15-0 kV charge at collection drum, 16-22 g blunt end needle, 0.02-0.15 mL/min flow rate, and 5-15" tip-to-collector distance.

Example 28

Properties of Typical Non-Woven Microfibrous Fabrics Prepared by Electrospinning Electrospun fabrics prepared as described above were analyzed and found to have the following properties (see Table VI).

TABLE I

Synthesis and Properties of Copolymers P-I-A to P-I-I

| Polymer Number | Composition of Charge | | | | GPC[c] Data | | | DSC Data | |
|---|---|---|---|---|---|---|---|---|---|
| | PEG $M_n$, kD | PEG/ Polyester, (wt) | Monomer Types & Molar Ratios[a] | Catalyst M/C[b] | Mn, kDa | Mw, kDa | IV[d] | Tm, °C. | $\Delta H_f$, J/g |
| P-I-A | 20 | 6/94 | 92/8 G/TMC | 16000 | e | e | 1.50 | 223 | 105 |
| P-I-B | 35 | 6/94 | 92/8 G/TMC | 14000 | e | e | 1.39 | 47, 224 | 12, 78 |
| P-I-C | 35 | 10/90 | 70/30 G/CL | 8000 | e | e | 1.79 | 50, 127, 223 | 12, 6, 78 |
| P-I-D | 20 | 10/90 | 70/30 G/CL | 16000 | e | e | 1.79 | 46, 218 | 2, 65 |
| P-I-E | 35 | 15/85 | 70/30 G/CL | 10000 | e | e | 1.51 | 55, 128, 211 | 11, 15, 31 |
| P-I-F | 11 | 7/93 | 95/5 LL/TMC | 3000 | 126 | 245 | (1.72) | 51, 154 | 6, 15 |
| P-I-G | 14 | 9/91 | 95/5 LL/TMC | 3000 | 51 | 157 | (0.68) | 149 | 35 |
| P-I-H | 20 | 13/87 | 95/5 LL/TMC | 3000 | 86 | 203 | (1.45) | 43, 157 | 10, 35 |
| P-I-I | 11 | 9/91 | 95/5 LL/TMC | 3000 | 109 | 257 | (1.51) | 47, 160 | 3, 26 |

[a]G = Glycolide; TMC = trimethylene carbonate; CL = ε-caprolactone; LL = l-lactide.
[b]Molar ratio of monomer to stannous octanoate.
[c]Gel permeation chromatography in CH$_2$Cl$_2$.
[d]Inherent viscosity in HFIP (in CHCl$_3$).
e Insoluble in CH$_2$Cl$_2$.

TABLE II

Synthesis and Properties of Copolymers P-II-A to P-II-D

| Polymer Number | Composition of Charge | | | | GPC[c] Data | | | DSC Data | |
|---|---|---|---|---|---|---|---|---|---|
| | Polyether Type[a]/ $M_n$, kD | Polyether/ Polyester, (wt) | Monomer Types & Molar Ratios[a] | Catalyst M/C[b] | Mn, kDa | Mw, kDa | IV[d] | Tm, °C. | $\Delta H_f$, J/g |
| P-II-A | ran/12 | 5/95 | 70/30 G/CL | 8000 | e | e | 1.95 | 124 | 26 |
| P-II-B | ran/12 | 10/90 | 70/30 G/CL | 8000 | e | e | 1.26 | 125, 217 | 7, 37 |
| P-II-C | blk/15 | 10/90 | 70/30 G/CL | 8000 | e | e | 1.53 | 130, 220 | 6, 35 |
| P-II-D | ran/12 | 5/95 | 96/4 LL/TMC | 5000 | 107 | 270 | (1.78) | 181 | 81 |

[a]ran = random; blk = block
[b]G = Glycolide; TMC = trimethylene carbonate; CL = ε-caprolactone; LL = l-lactide.
[c]Molar ratio of monomer to stannous octanoate.
[d]Gel permeation chromatography in CH$_2$Cl$_2$.
e Inherent viscosity in HFIP (in CHCl$_3$).
[f]Insoluble in CH$_2$Cl$_2$.

TABLE III

Synthesis and Properties of Copolymers P-III-A to P-III-G

| Polymer Number P-III- | PEG $M_n$, kD | PEG/Low Tg Segment/ Polyester, (wt) | Low Tg Segment Monomer Types & Molar Ratios[a] | Polyester Monomer Types & molar ratios[a] | Catalyst M/C[b] | GPC[c] Data Mn, kDa | Mw, kDa | IV[d] | DSC Data Tm, °C | ΔH$_f$, J/g |
|---|---|---|---|---|---|---|---|---|---|---|
| A | 20 | 9/16/75 | 85/15 CL/LL | 96/4 LL/CL | 3k | 98 | 203 | 1.49 | 43, 174 | 6, 56 |
| B | 11 | 10/43/47 | 60/24/16 CL/TMC/G | 81/19 LL/G | 6k | 65 | 130 | 1.29 | 104 | 6 |
| C | 35 | 20/10/70 | 97/3 TMC/CL | 96/4 LL/CL | 3k | 95 | 180 | 1.28 | 42, 158 | 9, 24 |
| D | 20 | 23/2/75 | TMC | 96/4 LL/CL | 3k | 69 | 150 | 0.97 | 41, 156 | 11, 25 |
| E | 35 | 25/10/65 | 97/3 TMC/CL | 96/4 LL/CL | 3k | 78 | 163 | 1.13 | 45, 150 | 21, 20 |
| F | 35 | 30/5/65 | 97/3 TMC/CL | 96/4 LL/CL | 3k | 75 | 155 | 0.98 | 51, 141 | 22, 19 |
| G | 35 | 35/5/60 | 97/3 TMC/CL | 96/4 LL/CL | 2k | 74 | 150 | 1.08 | 53, 145 | 30, 23 |

[a] G = Glycolide; TMC = trimethylene carbonate; CL = ε-caprolactone; LL = l-lactide.
[b] Molar ratio of monomer to stannous octanoate.
[c] Gel permeation chromatography in $CH_2Cl_2$.
[d] Inherent viscosity in $CHCl_3$.

TABLE IV

Extrusion and Processing Conditions of Typical Monofilaments

| Polymer No. | $T_m$ | Zone 1 | Zone 2 | Zone 3 | Spin-head | Orientation Scheme Draw Ratio/Temp, °C |
|---|---|---|---|---|---|---|
| P-I-D | 46, 218 | 140 | 175 | 228 | 230 | 5-6 X @ 45-60 |
| P-II-A | 124 | 140 | 177 | 228 | 230 | 5-6 X @ 45-60 |
| P-III-C | 42, 158 | 130 | 168 | 207 | 210 | 6-8 X @ 55-70 |
| P-III-E | 45, 150 | 130 | 165 | 208 | 210 | 6-10 X @ 45-60 |

TABLE V

Suture Properties of Typical Monofilaments

| Polymer Number | P-I-D (USG9) | P-II-A (USG10) | P-III-C (USL5) | P-III-E (USL6) |
|---|---|---|---|---|
| Physical Properties | | | | |
| Diameter, mm | 0.45 | 0.46 | 0.28 | 0.28 |
| Initial Strength, Kpsi | 56.9 | 67.8 | 45.3 | 35.9 |
| N | 65.6 | 78.7 | 19.5 | 15.9 |
| Modulus, Kpsi | 21 | 50 | 256 | 153 |
| Elongation, % | 109 | 103 | 99 | 137 |
| Knot Strength, N | 52.9 | 53.7 | 17.7 | 14.4 |
| Water Absorption/Swelling Data | | | | |
| Increase in Diameter, %/hour | 2.6/1, 4.5/18 | 1.1/1, 2.1/18 | 8.4/1 | 12.9/1 |
| Increase in volume, %/hour | 5.3/1, 9.1/18 | 2.2/1, 4.3/18 | 17.14/1 | 27.4/1 |
| In Vitro BSR, % @ Day 3 | 76 | 79 | — | — |
| Week 1 | 35 | 53 | 69 | 57 |
| Week 2 | 3 | 16 | 57 | 52 |
| Week 3 | — | — | 50 | — |
| In Vivo BSR, % @ Week 1 (traditional polyester of similar composition) | 45 (62) | 61 (62) | — | — |
| Week 2 (traditional polyester of similar composition) | 6 (30) | 30 (30) | — | — |

TABLE V-continued

Suture Properties of Typical Monofilaments

| Polymer Number | P-I-D (USG9) | P-II-A (USG10) | P-III-C (USL5) | P-III-E (USL6) |
|---|---|---|---|---|
| Accelerated In Vitro Mass Loss, Time to ~50% Mass Loss (traditional polyester of similar composition) | 6 hours (9 days) | 2.5 days (9 days) | — | — |

TABLE VI

Properties of Electrospun Fabrics Prepared from Typical Block Copolymers

| Polymer | Thermal Characteristics | | | Burst Strength (N/mm) | Deflection at Burst (mm) | Contact Angle (°) | Inherent Viscosity (dL/g) |
|---|---|---|---|---|---|---|---|
| | $T_g$ (°C.) | $\Delta H_f$ (J/g) | $T_m$ (°C.) | | | | |
| P-I-F | 71 | 22.8 | 158 | 100 | 25 | 131 | 1.52 |
| P-I-G | 60 | 30.6 | 158 | 61 | 24 | 135 | 0.99 |
| P-I-H | 63 | 28.7 | 159 | 48 | 33 | 137 | 1.43 |
| P-I-I | 61 | 28.7 | 159 | 104 | 27 | 121 | 1.51 |

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A swellable, absorbable, fiber- or microfiber-forming, high molecular weight, crystalline polyether-ester comprising: a polyether chain component with a molecular weight of more than about 11 kDa; an inherent viscosity of at least 0.8 dL/g in chloroform or hexafluoroisopropyl alcohol; a heat of fusion of greater than 5 J/g; wherein fibers or microfibers formed therefrom undergo at least 0.5% increase in their cross-sectional area when placed in an aqueous environment for less than three (3) hours; and wherein the polyether-ester comprises a pentablock polymer having a central polyether glycol block interlinked with polyester end blocks via low Tg polymer segments.

2. The swellable, absorbable, fiber- or microfiber-forming, high molecular weight, crystalline polyether-ester of claim 1, wherein the Tg polymer segments are synthesized from cyclic monomers and wherein the cyclic monomers comprise trimethylene carbonate, ϵ-caprolactone, or mixtures thereof.

3. The swellable, absorbable, fiber- or microfiber-forming, high molecular weight, crystalline polyether-ester of claim 1, wherein the polyester-ether comprises a multifilament yarn processed into a compressible, microporous felt for use as a scaffold for tissue engineering.

4. The swellable, absorbable, fiber- or microfiber-forming, high molecular weight, crystalline polyether-ester of claim 3, wherein the compressible felt comprises an absorbable coating, the coating containing at least one bioactive agent selected from antimicrobial agents, antineoplastic agents, and tissue growth promoting agents.

5. The swellable, absorbable, fiber- or microfiber-forming, high molecular weight, crystalline polyether-ester of claim 1, the polyether ester comprises a non-woven, microporous, microfibrous fabric made by electrostatic spinning.

6. The swellable, absorbable, fiber- or microfiber-forming, high molecular weight, crystalline polyether-ester of claim 5, wherein the non-woven, microporous, microfibrous fabric comprises an absorbable coating, the coating containing at least one bioactive agent selected from antimicrobial agents, antineoplastic agents, and tissue growth promoting agents.

7. The swellable, absorbable, fiber- or microfiber-forming, high molecular weight, crystalline polyether-ester of claim 1, comprising a melt-spun monofilament yarn for use as a surgical suture.

8. The swellable, absorbable, fiber- or microfiber-forming, high molecular weight, crystalline polyether-ester of claim 7, wherein the melt-spun monofilament yarn has a breaking strength of more than 30 kpsi and a modulus of less than 300 kpsi.

9. The swellable, absorbable, fiber- or microfiber-forming, high molecular weight, crystalline polyether-ester of claim 7, wherein the monofilament suture has an absorbable coating, the coating containing at least one bioactive agent selected from antimicrobial agents, antineoplastic agents, and tissue growth promoting agents.

10. The swellable, absorbable, fiber- or microfiber-forming, high molecular weight, crystalline polyether-ester of claim 9, wherein the low Tg polymer segment is derived from at least one cyclic monomer.

11. The swellable, absorbable, fiber- or microfiber-forming, high molecular weight, crystalline polyether-ester of claim 10, wherein the cyclic monomer is selected from the group consisting of l-lactide, ϵ-caprolactone, p-dioxanone, trimethylene carbonate, morpholinedione and mixtures thereof.

12. A swellable, absorbable, fiber- or microfiber-forming, high molecular weight, crystalline polyether-ester comprising: a polyether chain component with a molecular weight of more than about 11 kDa; an inherent viscosity of at least 0.8 dL/g in chloroform or hexafluoroisopropyl alcohol; a heat of fusion of greater than 5 J/g; wherein fibers or microfibers formed therefrom undergo at least 0.5% increase in their cross-sectional area when placed in an aqueous environment for less than three (3) hours; wherein the polyether-ester is end-grafted with at least one cyclic monomer selected from the group consisting of l-lactide, glycolide, ϵ-caprolactone, p-dioxanone, trimethylene carbonate, morpholinedione and mixtures thereof and wherein the polyether-ester comprises a triblock copolymer having a central polyether glycol block and each end block comprising a low Tg polymer segment.

\* \* \* \* \*